United States Patent
Acharya et al.

(10) Patent No.: US 11,721,339 B2
(45) Date of Patent: Aug. 8, 2023

(54) MESSAGE FILTERING BASED ON DYNAMIC VOICE-ACTIVATED RULES

(71) Applicant: Stryker Corporation, Kalamazoo, MI (US)

(72) Inventors: Sridhar Acharya, Fremont, CA (US); Arun Mirchandani, Pleasanton, CA (US)

(73) Assignee: Stryker Corporation, Kalamazoo, MI (US)

( * ) Notice: Subject to any disclaimer, the term of this patent is extended or adjusted under 35 U.S.C. 154(b) by 328 days.

(21) Appl. No.: 17/033,843

(22) Filed: Sep. 27, 2020

(65) Prior Publication Data

US 2022/0101843 A1 Mar. 31, 2022

(51) Int. Cl.
*G10L 15/22* (2006.01)
*G10L 15/18* (2013.01)
*H04L 51/212* (2022.01)

(52) U.S. Cl.
CPC .......... *G10L 15/22* (2013.01); *G10L 15/1822* (2013.01); *H04L 51/212* (2022.05)

(58) Field of Classification Search
USPC ............. 704/231, 246, 247, 251, 252, 275
See application file for complete search history.

(56) References Cited

U.S. PATENT DOCUMENTS

| | | |
|---|---|---|
| 5,576,952 A | 11/1996 | Stutman et al. |
| 7,034,691 B1 | 4/2006 | Rapaport et al. |
| 9,149,190 B2 | 10/2015 | Mayoras, Jr. |
| 9,652,960 B2 | 5/2017 | Flinsenberg et al. |
| 9,740,825 B2 | 8/2017 | Sansale et al. |
| 10,025,905 B2 | 8/2018 | Dantsker et al. |
| 10,057,732 B2 | 8/2018 | Soomro |
| 10,153,994 B2 | 12/2018 | Mancine et al. |
| 11,069,351 B1 * | 7/2021 | Menon ............. G06F 40/30 |
| 2005/0071190 A1 | 3/2005 | Herger et al. |
| 2007/0067185 A1 | 3/2007 | Halsted |

(Continued)

FOREIGN PATENT DOCUMENTS

| | | |
|---|---|---|
| EP | 3588511 A1 | 1/2020 |
| GB | 2517259 A | 11/2014 |

(Continued)

OTHER PUBLICATIONS

Spok, "Improving Patient Care While Saving Time for Physicians", 10 pages, retrieved on Sep. 28, 2020 from: https://www.spok.com/solutions/healthcare-solutions-role/physicians/#information.

(Continued)

*Primary Examiner* — Leonard Saint-Cyr
(74) *Attorney, Agent, or Firm* — McDonnell Boehnen, Hulbert & Berghoff LLP

(57) ABSTRACT

Embodiments include methods, devices, systems, and non-transitory process-readable storage media for voice-activated message filtering rule generation. Some embodiments may include receiving a spoken command from a communication device, parsing the spoken command to identify an element of the spoken command, generating a message rule based on the identified element of the spoken command, determining whether the generated message rule has been met, and sending a message to the communication device in response to determining that the message rule has been met.

57 Claims, 10 Drawing Sheets

(56) References Cited

U.S. PATENT DOCUMENTS

| | | | |
|---|---|---|---|
| 2007/0083403 A1 | 4/2007 | Baldwin et al. | |
| 2007/0168223 A1 | 7/2007 | Fors et al. | |
| 2008/0114689 A1 | 5/2008 | Psynik et al. | |
| 2012/0136221 A1 | 5/2012 | Killen et al. | |
| 2012/0191466 A1 | 7/2012 | Quint et al. | |
| 2012/0290311 A1 | 11/2012 | Tara et al. | |
| 2013/0113616 A1 | 5/2013 | Pinel et al. | |
| 2014/0244277 A1 | 8/2014 | Krishna Rao et al. | |
| 2015/0222450 A1* | 8/2015 | Ko | G08C 17/02 340/5.82 |
| 2015/0286787 A1 | 10/2015 | Chen et al. | |
| 2017/0053552 A1 | 2/2017 | Zhong et al. | |
| 2018/0197638 A1 | 7/2018 | Blanshard et al. | |
| 2018/0211656 A1 | 7/2018 | Chong et al. | |
| 2018/0285752 A1* | 10/2018 | Yu | G06N 5/04 |
| 2019/0004692 A1 | 1/2019 | Mason | |
| 2019/0156937 A1 | 5/2019 | Shimomura et al. | |
| 2019/0207857 A1 | 7/2019 | Shelton et al. | |
| 2019/0304455 A1* | 10/2019 | Jaygarl | G10L 15/08 |
| 2019/0362624 A1 | 11/2019 | Shin et al. | |

FOREIGN PATENT DOCUMENTS

| | | |
|---|---|---|
| JP | 2019525337 A | 9/2019 |
| WO | 2007058821 A2 | 5/2007 |
| WO | 2010023409 A1 | 3/2010 |
| WO | 2010141802 A1 | 12/2010 |
| WO | 2012060899 A2 | 5/2012 |
| WO | 2013134639 A2 | 9/2013 |

OTHER PUBLICATIONS

"Integrate Patient Information with Workflow to Deliver Better Patient Care", System Integration and Interoperability, Vocera, 5 pages, retrieved on Sep. 28, 2020 from: https://www.vocera.com/nz/products/integrations-alerts-alarms.

"Adopting Fast Lane in Clinical Communications" Jun. 2017, Cisco Validated Design, PatientSafe Solutions, 29 pages, retrieved from: https://www.cisco.com/c/dam/en/us/td/docs/solutions/CVD/Healthcare/CVD-Adopting-FastLane-Clinical-Comm-PatientSafe-2017JUN.pdf.

Pathinarupothi et al., "Data to diagnosis in global health: a 3P approach", BMC Medical Informatics and Decision Making, 18, Article No. 78 (Sep. 2018), 37 pages, retrieved from: https://bmcmedinformdecismak.biomedcentral.com/articles/10.1186/s12911-018-0658-y.

Spok, "Drive action by connecting clinical teams with the people and information they need when and where it matters most", Clinical Care, 6 pages, retrieved on Sep. 28, 2020 from: https://www.spok.com/solutions/clinical-alerting-notification/.

Philips, Clinical services, Clinical Alarm Management | Philips Healthcare, 6 pages, retrieved on Sep. 28, 2020 from: https://www.philips.co.in/healthcare/clinical-solutions/alarm-management.

"Improving collaboration in healthcare: 5 ways mobile can help", Published May 30, 2019, by Taylor Mallory Holland, retrieved from: https://insights.samsung.com/2019/05/30/improving-collaboration-in-healthcare-5-ways-mobile-can-help/.

Korean Intellectual Property Office, International Search Report and Written Opinion in International Application No. PCT/US2021/051412 dated Jan. 11, 2022 (18 pages).

* cited by examiner

MESSAGE FILTERING BASED ON DYNAMIC VOICE-ACTIVATED RULES

BACKGROUND

Wireless communication systems are increasingly utilized to facilitate coordination among workgroups in a variety of environments. Wireless communication systems have proven highly effective in hospitals and other healthcare environments, because mobile communicators enable rapid communication among doctors, nurses, and other care team staff who sometimes must provide time-critical patient care. Healthcare environments can be busy, information rich, stressful and distracting.

Care providers receive a torrent of information and requests for their attention. Messages, calls, alerts ages, voice calls, mass messages, and public announcements demanding caregiver attention may range from the mundane to time-critical emergencies involving the life or health of patients. Relying on others to indicate the urgency of a given message is unreliable because the sender may not properly indicate the urgency of a message, may bury critical information in a long message, and further may have little or no insight into the care provider's patients, tasks, or other responsibilities. Thus, care providers must review each message carefully to manually identify those that are most urgent, a task that can be time-consuming and may not be accomplished when a care provider is engaged in an important activity. As a result, there is a risk that a care provider may miss an important or urgent message.

SUMMARY

Various embodiments provide methods, systems, wireless communication devices, and non-transitory process-readable storage media for enabling a communication system to generate a message rule based on a dynamic voice command received by a communication device. The message rule may be dynamically generated and applied on a per-user basis. The communication system may selectively send a message to the communication device based on a message rule.

Various embodiments include methods and server devices configured to perform methods that include receiving a spoken command from a communication device, parsing the spoken command to identify an element of the spoken command, generating a message rule based on the identified element of the spoken command, determining whether the generated message rule has been met, and sending a message to the communication device in response to determining that the message rule has been met.

Some embodiments may include determining an intent including an action to be taken and a subject of the action based on the identified element of the spoken command. In some embodiments, generating the message rule based on the identified element of the spoken command may include generating the message rule based on the determined intent. In some embodiments, generating the message rule based on the identified element of the spoken command may include adding one or more rule fields to the determined intent, and generating the message rule based on the determined intent and the added one or more rule fields.

In some embodiments, generating the message rule based on the identified element of the spoken command may include generating the message rule including a patient event. In some embodiments, generating the message rule based on the identified element of the spoken command may include generating the message rule comprising a patient event and a patient event threshold. In some embodiments, generating the message rule based on the identified element of the spoken command may include generating the message rule comprising a patient event and a qualifier of the patient event.

Some embodiments may include refraining from sending the message to the communication device in response to determining that the message rule has not been met. In some embodiments, generating the message rule based on the identified element of the spoken command may include mapping the identified element to a rule template field, and generating the message rule based on information in the rule template field.

In some embodiments, mapping the identified element to the rule template field may include converting information in the identified element to a field value, and generating the message rule based on information in the rule template field may include generating the message rule based on information in the field value. In some embodiments, mapping the identified element to the rule template field may include mapping a patient vital sign identifier to the rule template field. In some embodiments, mapping the identified element to the rule template field may include mapping a comparator to the rule template field. In some embodiments, mapping the identified element to the rule template field may include mapping a patient vital sign value to the rule template field. In some embodiments, mapping the identified element to the rule template field may include applying a customized mapping of the identified element and the rule template field.

Some embodiments may include determining a priority based on the identified element of the spoken command, wherein generating the message rule based on the identified element of the spoken command may include associating the message rule with the determined priority. Some embodiments may include sending to the communication device a summary of the identified element from the spoken command, and monitoring for an approval from the communication device of the summary of the identified element from the spoken command. In such embodiments, generating the message rule based on the identified element of the spoken command may include generating the message rule based on identified elements of the spoken command in response to receiving the approval from the communication device of the summary of the identified element from the spoken command.

Some embodiments may include sending to the communication device a summary of the generated message rule, and monitoring for an approval from the communication device of the summary of the generated message rule. In such embodiments, determining whether the generated message rule has been met may include determining whether the generated message rule has been met in response to receiving an approval from the communication device of the summary of the generated message rule.

Some embodiments may include generating a time to live value for the generated message rule, and deleting the message rule after the time to live value is met. Some embodiments may include receiving a second spoken command from the communication device, parsing the second spoken command to identify an element in the second spoken command that relate to modifying the message rule, and modifying the message rule based on the identified element in the second spoken command.

Further embodiments include a communication device having a processor configured with processor-executable instructions to perform operations of any of the methods summarized above. Further embodiments include a non-transitory processor-readable medium on which is stored processor-executable instructions configured to cause a processor of a communication device to perform operations of any of the methods summarized above. Further embodiments include a communication device having means for performing functions of any of the methods summarized above.

BRIEF DESCRIPTION OF THE DRAWINGS

The accompanying drawings, which are incorporated herein and constitute part of this specification, illustrate exemplary embodiments of the invention, and together with the general description given above and the detailed description given below, serve to explain the features of the invention.

DETAILED DESCRIPTION

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

Various embodiments provide methods, systems, wireless communication devices, and non-transitory process-readable storage media for enabling a communication device that receives a variety of types of messages to provide an automatically prioritized display of the messages. As used herein, the term "message" refers to any of a variety of messages that the communication device may receive, including phone calls (e.g., voice calls), email messages, text messages, alert messages, notifications, tasks, action assignment messages, and the like.

Figure 5:
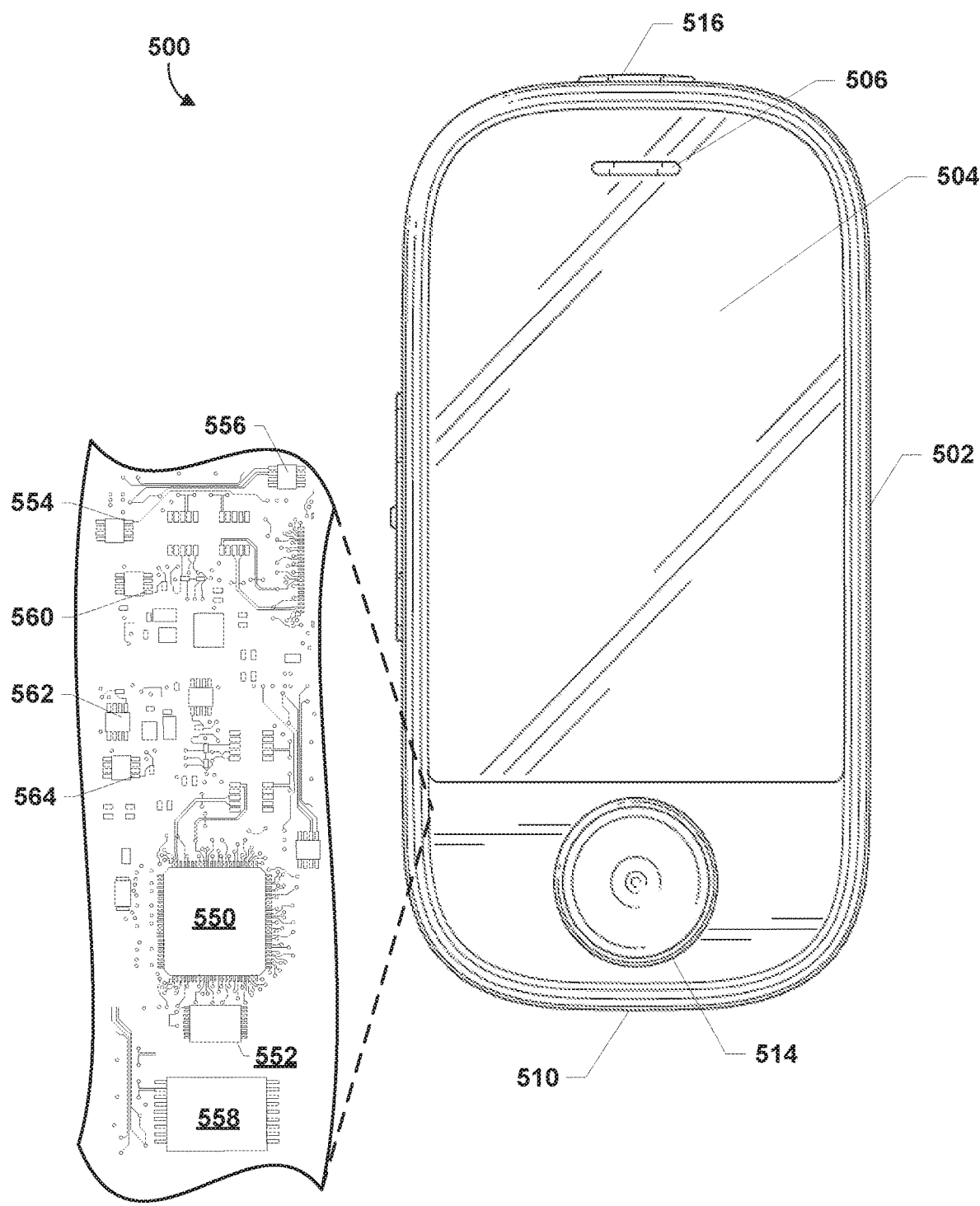
FIG. 5 illustrates a communication device suitable for use in various embodiments.

The term "communication device" is used herein to refer to an electronic device equipped with at least a processor and a transceiver configured to support wireless communications with a wireless local area network (WLAN). Examples of communication devices include mobile devices, particularly communicators for use within a hospital or other healthcare environments. In various embodiments, communication devices may be configured with memory or storage as well as networking capabilities, such as network transceiver(s) and antenna(s) configured to establish a WLAN connection with an access point. Communication devices may also include voice communications badge devices, an example of which is illustrated in FIG. 5.

As noted above, healthcare providers work in busy environments and may be bombarded with information and requests for their attention ranging from mundane communications to urgent communications involving the life or health of a patient. Some messages may have little or no relation to a care provider's patients or tasks. Requiring users to manually sort messages to identify those that are important or urgent creates a risk that a user working in a busy and stressful environment may miss an important or urgent message, with negative consequences on patient care and outcomes.

Various embodiments enable a communication system to generate a message rule based on a voice command spoken by a user that is received from a communication device. The communication system may generate a message rule dynamically and apply the message rule on a per-user basis. The communication system may apply a message rule to determine whether to send a message to the communication device. The message rule may be applied for a period of time after which application of the rule by the communication system may be suspended. The message rule may be dynamically updated, changed, or deleted.

In various embodiments, the server device may receive a spoken command from a communication device a communication network. In some embodiments, the server device may receive a digitization of the spoken command. In some embodiments, the communication device may record the spoken command and generate a file, such as a digital recording in an appropriate format, for example, MP3, WAV, AAC, FLAC, OGG, WMA, or any other suitable format. In such embodiments, the communication device may send the generated file to the server device. In some embodiments, the communication device may temporarily store (e.g., buffer) a recording of the spoken command and send the recording of the spoken command to the server device in a bit stream, in an audio file, in audio data packets, or another suitable transmission method.

In some embodiments, the server device may parse the spoken command to identify an element of the spoken command. An element of the spoken command may include a subject of the command, an object of the command, an action to be performed, a time period or duration, or a time deadline. An element of the spoken command may include a threshold condition, such as a vital sign being greater than, less than, or equal to a vital sign threshold, the performance or non-performance of an action, or the occurrence or non-occurrence of an event. An element of the spoken command may include a word that functions as a conjunction, preposition, adverb, qualifier, modifier, or emphasizer. Examples of a spoken command may include:

"Let me know when Lisa Reilly's heart rate exceeds 100 beats per minute."

"Let me know urgently when Lisa Reilly's heart rate exceeds 100 beats per minute and hemoglobin goes below 6."

"Notify me right away when Lisa Reilly is brought back to med-surg." ("Med-surg" refers to medical-surgical unit of a hospital or other care facility.)

"Tell me when Lisa Reilly's nurse rounds are done." (That is, when a nurse has performed rounds for patient Lisa Reilly.)

"I need to know when Lisa Reilly's hemoglobin goes below 6."

"Stop sending me alerts for Lisa Reilly."

"Send me alerts only for Lisa Reilly."

"Let me know if a note is entered into Lisa Reilly's chart."

"Notify me if anyone enters a new prescription for Lisa Reilly."

"Tell me when Lisa Reilly's surgery is done."

"Notify me when Lisa Reilly is brought to recovery."

"Notify me when Lisa Reilly brought back to her room."

"Let me know when Lisa Reilly is discharged."

"Tell me when Lisa Reilly has been visited by her cardiologist."

"Tell me Lisa Reilly's heartrate and temperature every 15 minutes."

"Until 12:00 AM, notify me if Lisa Reilly's heart rate exceeds 100 beats per minute."

"Cancel all rules for Lisa Reilly."

"Alert me when Lisa Reilly's systolic blood pressure exceeds 180"

For example, the server device may parse the spoken command "Let me know when Lisa Reilly's heart rate exceeds 100 beats per minute" and identify as speech elements "let me know," "when," "Lisa Reilly's," "heart rate," "exceeds," and "100 beats per minute." To accomplish such parsing, the server device may apply a language parsing function, such as a natural language processing function, to identify speech elements in the spoken command.

In some embodiments, the server device may generate a message rule based on the identified element of the spoken command. For example, using the elements "let me know," "when," "Lisa Reilly's," "heart rate," "exceeds," and "100 beats per minute," the server device may generate a message rule that prompts the server device to send a message to the communication device in response to determining that Lisa Reilly's heart rate exceeds 100 beats per minute. Implementing such a rule, the server device may not send messages to the communication device based on heart rate readings less than 100 beats per minute, thus filtering some messages that might otherwise have been sent to the communication device.

In some embodiments, the server device may generate a message rule that includes a patient event, for example, a patient condition, a vital sign, a change in any medical data or any patient status, an action taken related to the patient, an action performed by another care provider related to the patient, and any other suitable information (sometimes referred to as a "patient context" or "context information"). In some embodiments, the server device may generate a message rule that a patient event and a patient event threshold (e.g., "exceeds 100 beats per minute"). In some embodiments, the server device may generate a message rule that includes a patient event and a qualifier of the patient event. Examples of a qualifier include "urgently," "right away," "only," "except," and other suitable qualifiers. For example, the spoken command "Send me alerts only for Lisa Reilly" may include the qualifier "only." As another example, "Stop sending me alerts except for alerts about Lisa Reilly" may include the qualifier "except." Other examples are also possible.

In some embodiments the server device may add units for a particular measure. For example, the server device may parse the spoken command "Alert me when Lisa Reilly's systolic blood pressure exceeds 180" and in doing so, identify the elements "blood pressure" and "180." In response to identifying these elements, the server device may associate a unit "millimeters of mercury" or "mmHg" to the element "180" for accuracy and clarity, as those units correspond to blood pressure measurements. As another example, the server device may add "BPM" or beats per minute in response to identifying "HR" or "heart rate" in the spoken command. As a further example, the server device may add "° F." or "° C." for degrees Fahrenheit or degrees Celsius in response to identifying the word "temperature" or "temp" in the spoken command. Other commonly used metric and English units may be similarly added.

In some embodiments, the server device may determine whether the generated message rule has been met (i.e., the conditions defined in the rule are satisfied). To do so, the server device may monitor a variety of data inputs related to a patient that may correlate to or define an event, such as a patient condition, a vital sign, a change in any medical data or any patient status, an action taken related to the patient, an action performed by other care providers related to the patient, information received in a admit-discharge-transfer (ADT) feed, and other patient-related information (sometimes referred to as a "patient context" or "context information"). By evaluating on one or more patient events against a generated message rule, the server device may determine whether the message rule has been met.

In various embodiments, the server device may send a message to the communication device in response to determining that the message rule has been met. In various embodiments, the message sent to the communication device may include any form of message or notification, and may trigger the communication device to present any form of message or notification, which may include a text element, a visual elements, an audible element, a tactile elements, and/or any other suitable notification, including any combination of the foregoing. The server device may refrain from sending the message to the communication device in response to determining that the message rule has not been met. Thus, the rule may function as a filter on messages transmitted to the communication device.

In some embodiments, the server device may determine an intent based on the identified element of the spoken command. Generally, an intent is a word or a phrase that can be translated into an action. The intent may include, for example, an action to be taken and a subject of the action. The server device may use the intent, as well as other information in the spoken comment, to generate the message rule. For example, based on the elements "let me know," "when," "Lisa Reilly's," "heart rate," "exceeds," and "100 beats per minute," the server device may determine an intent that includes information that may be used to generate the message rule. The intent may include information such as a request identifier (e.g., let me know, notify me, send me a message, etc.), a recipient identifier (e.g., a user associated with the communication device), a patient identifier (e.g., Lisa Reilly, which may be separated into a first name identifier and a second name identifier), a medical record number (MRN), and various conditions, such as "heart rate", the value of "100 beats per minute), and a comparator or threshold (such as "exceeds," which may be converted to or interpreted as "is greater than"). In some embodiments, the intent may include a priority indicator based on one or more elements of the spoken command. For example, based on the presence of a priority indicator in an element, such as "urgently" or "right away," the server device may include in the intent an indication of a relatively higher priority (e.g., "urgent," or a numeric or symbolic expression thereof) as compared to a relatively lower priority (e.g., "normal," or a numeric or symbolic expression thereof). In some embodiments, the server device may generate the message rule based on the determined intent.

In some embodiments, the server device may add one or more rule fields to the determined intent, and generate the message rule based on the determined intent and the added rule fields. Such rule fields may include additional information that enable the generation of a message rule based on the determined intent. An example of additional information that may be provided in added rule fields include a symbol or code that enables the generation of a message rule based on the determined intent. For example, a rule field may include a symbol ">" in addition to or as an alternative to the element "is greater than." As another example, a rule field may include a code "HR" in addition to or as an alternative to the element "heart rate." As another example, a rule field may include a code indicating a value for presentation on a display (e.g., a display of the communication device), such as "value_display_view" or "comparator_display_view" for better readability and usability. In some embodiments, adding the one or more rule fields may function as a processing operation between identifying an element of the spoken command and generating the message rule.

In some embodiments, to generate the message rule based on the identified element of the spoken command, the server device may map the identified element to a rule template field. In some embodiments, a rule template field may include a field in a rule template for a specific piece of information. Examples of rule template fields include "[recipient]", "[patient_first_name]", "[patient_last_name]", Immr, "[vital]", and "[comparator]". In some embodiments, the server device may convert information in the identified element to a field value, and may generate the message rule based on information in the field value. For example, the server device may convert information from an element such as a vital sign to "[vital_display]" to signify a human-readable version of the vital sign, and "[vital_display_view]" to signify ease of viewing of entity names. As another example, the server device may convert information from an element such as a comparator to "[comparator_display]" to signify a human-readable version of the comparator, and "[comparator_display_view]" to signify ease of viewing the entity names. As another example, the server device may use a value (e.g., of a vital sign). In some cases, such as when a value contains a decimal, the server device may replace any decimals with underscores, and store the value as "[value_display_view]". As another example, the server device may convert "heart rate" to "HR", "blood pressure" to "BP", "less than" to "lt", "is below" to "lt", "goes below" to "lt", "greater than" to "gt", "exceeds" to "gt", and the like. In some embodiments, the server device different information in the identified element to the same field value.

In some embodiments, the server device may map a patient vital sign identifier to a rule template field. In some embodiments, the server device may map a comparator to a rule template field. In some embodiments, the server device may map a patient vital sign value to a rule template field. In some embodiments, the server device may apply a customized mapping of the identified element and the rule template field. In various embodiments, a mapping or set of mappings of information in an identified element to a rule template field may be customized for a user, for a set of users, or for any individual or group. In some embodiments, the server device may generate the message rule based on information in the field value.

In some embodiments, the server device may determine a priority based on the identified element of the spoken command, and may associate the message rule with the determined priority. For example, as noted above, based on the presence of a priority indicator in an element, such as "urgently" or "right away," the server device may determine an indication of a relatively higher priority (e.g., "urgent," or a numeric or symbolic expression thereof) as compared to a relatively lower priority (e.g., "normal," or a numeric or symbolic expression thereof). In some embodiments, based on the priority, the server device may associate a priority with a message, notification, or alert that the server device later sends to the communication device.

In some embodiments, the server device may send a message to the communication device to enable the user speaking the command to confirm the accuracy of an identified speech element and/or the generated message rule. In some embodiments, the server device may send a summary of the identified element from the spoken command to the communication device, and monitor for an approval or correction reply from the communication device. In such embodiments, the server device may generate the message rule based on identified elements of the spoken command in response to receiving approval of the summary of the identified element from the communication device. In some embodiments, the server device may send a summary of the generated message rule to the communication device, and monitor for an approval or correction reply from the communication device. In such embodiments, the server device may generate the message rule based on the identified element of the spoken command in response to receiving an approval from the communication device of the summary of the generated message rule.

In some embodiments, a generated message rule may be applied for a limited period of time. In some embodiments, the server device may generate a time to live value that indicates a duration or time period that the generated message rule should be implemented by the communication system. After the time to live value is met, the server device may delete the message rule, or suspend application of the message rule.

In some embodiments, the server device may modify or update a message rule based on a subsequent instruction or command. In some embodiments, the server device may receive a second spoken command from the communication device. In some embodiments, the server device may parse the second spoken command to identify an element in the second spoken command that relate to modifying the message rule, and may modify the message rule based on the identified element in the second spoken command.

Various embodiments improve the operation of a communication device and a communication system by providing messages based on dynamic message rules. In various embodiments, the message rules may be generated based on instructions from each individual user. Various embodiments improve the operation of the communication device and the communication system by relieving communication device users of the burden manually reviewing the content of each message delivered to the communication device, thereby reducing the risk that the user may miss an urgent or important message. Various implementations may be particularly useful in busy, high-stress environments such as health care environments.

Figure 1:
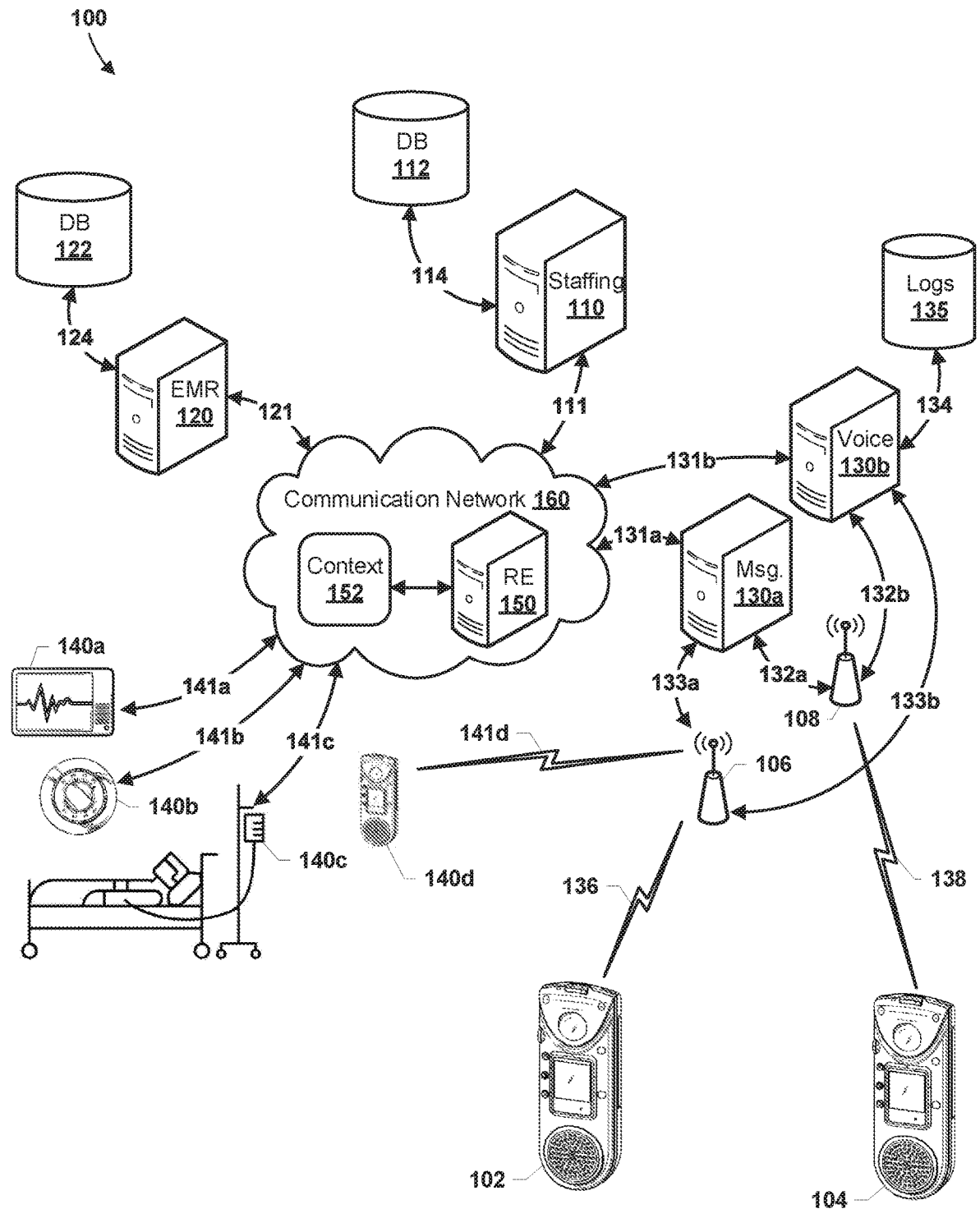
FIG. 1 is a component block diagram of a communication system suitable for use in various embodiments.

FIG. 1 illustrates a communication system 100 suitable for use with the various embodiments. The communication system 100 may include communication devices 102, 104, a staffing server 110, an electronic medical record (EMR) server 120, a messaging server 130a, a voice communications server 130b, one or more sensors/sources 140a-140d, and a rules engine 150. The various elements of the communication system 100 may be configured to communicate over a communication network 160 via wired or wireless communication links 111, 121, 131a, 131b, and 141a-141d. In some embodiments, one or more of the staffing server 110, the EMR server 120, the messaging server 130a, the voice communications server 130b, and the rules engine 150 may be configured as separate devices (e.g., server devices). In some embodiments, one or more of the staffing server 110, the EMR server 120, the messaging server 130a, the voice communications server 130b, and the rules engine 150 may be configured as separate logical services on one server or similar device.

The EMR server 120 may include one or more server computing devices configured to store, update, and transmit information such as patient-based data. The EMR server 120 may communicate over a wired or wireless communication link 124 with a database 122 configured to store data records. Patient-based data may include identifiers or codes indicating an identity of a patient, health care personnel associated with the patient (e.g., physician, specialist, hospitalist, nurse, etc.), patient location information (e.g., room, bed, wing, building), a status of the patient (e.g., discharged, admitted, etc.), and other suitable information.

The EMR server 120 may transmit messages (e.g., in HL7 or another suitable format) including patient-based data via one or more information feeds. In some embodiments, the EMR server 120 may transmit the messages on the occurrence of an event that changes the patient-based data at the EMR server 120. For example, the EMR server 120 may transmit a message that indicates a patient identifier and a room identifier in response to the patient corresponding to the patient identifier being admitted to the hospital and being assigned to a room corresponding to the room identifier.

In some embodiments, the EMR server 120 may be connected to or otherwise may utilize a system capable of sending and receiving HL7 version 2.3 messages (e.g., admission, discharge, transfer (ADT) messages), such as messages that include a role (or "ROL") segment that indicates care team assignment information. The EMR server 120 may transmit information (e.g., in HL7, ADT messaging, or another suitable format) via one or more information feeds (e.g., to the rules engine 150).

The staffing server 110 may be one or more server computing devices configured to at least synchronize care team assignment data from different systems related to the hospital. The staffing server 110 may communicate over a wired or wireless communication link 114 with a database 112 configured to store data records. The staffing server 110 may transmit information (e.g., in HL7, ADT messaging, or another suitable format) via one or more information feeds (e.g., to the rules engine 150).

In some embodiments, the staffing server 110 may be configured to continually receive data from the EMR server 120, the messaging server 130a, the voice communications server 130b, and/or other systems that indicate staffing changes (e.g., to care teams associated with the various patients, locations, and/or shifts of the hospital). For example, the staffing server 110 may receive subscription messages from the voice communications server 130a, 13b indicating when particular nurses of the hospital log-in or out of a shift and/or HL7 messages from the EMR server 120 that indicate when a particular patient's data changes (e.g., assigned to a new bed, room, specialist doctor, etc.). The data records may include, e.g., records related to the various patients admitted to a hospital and/or the various care teams active in the hospital, and may be accessed to obtain a data record indicating the last known nurse, nurse assistant, bed, wing, building, physician, specialist, and hospitalist for a particular patient identifier.

The messaging server 130a may include one or more server computing devices configured to control various messages sent between the communication devices 102, 104 via access points 106, 108. In some embodiments, the messaging server 130a may be configured to control messages sent to the communication devices 102, 104 from the rules engine 150.

The voice communications server 130b may include one or more server computing devices configured to control various voice calls placed between the communication devices 102, 104 via access points 106, 108. In some embodiments, the voice communications server 130b may include a signaling gateway service to facilitate communications between and among the communication devices 102, 104 and the voice communications server 130b, such as login functions, voice call functions, and other suitable functions. In some embodiments, the signaling gateway service may be configured as a separate device (not illustrated).

In some embodiments, the voice communications server 130b may be configured to receive and parse voice commands received from the communication devices 102, 104. In some embodiments, the voice communications server 130b may be configured with functions including an automatic speech recognition broker, a data structuring engine, a speech-to-text function, a natural language processing function, an intent generator, and other suitable functions.

As noted above, in various embodiments, the messaging server 130a and the voice communications server 130b may be configured as separate devices, or as logical functions in one device. In some embodiments, the messaging server 130a and the voice communications server may transmit information in a suitable format via one or more information feeds (e.g., to the rules engine 150).

In operation, the communication system 100 may include a large number of communication devices and access points, illustrated as communication devices 102, 104, 140d and access points 106, 108 for conciseness. The communication devices 102, 104, 140d may communicate with an access point 106, 108 over separate wireless communication links 136, 138, 141d. The access points 106, 108 may communicate with the voice communications server 130a, 130b over separate communication links 132a, 132b, 133a, 133b. The voice communications server 130a, 130b may control various messages and voice calls placed between the communication devices 102, 104, 140d. The voice communications server 130a, 130b may communicate over a wired or wireless communication link 134 with a database 135 configured to store logs and other data records.

In some embodiments, the voice communications server 130b may be configured to provide information to the rules engine 150 via one or more information feeds. For example, the voice communications server 130b may store, update, and transmit at least shift-based and/or location-based data of the various care team assignments of the hospital. The voice communications server 130b may also store, update, and transmit patient-related information, information related to the facility or environment, and other information. For example, the voice communications server 130b may receive messages from any of the communication devices 102, 104 that indicate users of the communication devices 102, 104, 140d have logged-out of or logged-into a shift of working in a care team at the hospital. As another example, the voice communications server 130b may receive a message from a communication device 102, 104, 140d regarding the condition of a patient, equipment, a location, an environmental condition, or other suitable information. The voice communications server 130b may transmit information in a suitable format via one or more information feeds (e.g., to the rules engine 150).

The one or more sensors/sources 140a-140d may include one or more sensor devices to sense information about a patient, an environment, or other suitable information. The one or more sensors/sources 140a-140d may further include one or more sources information about a patient, an environment, or other suitable information, such as a bed exit monitor, a nurse call button/system, a video surveillance system, or another suitable source). For example, patient monitors 140a, 140c may include devices configured to monitor one or more patient conditions or vital signs. In some embodiments, the one or more sensors/sources 140a-140d may transmit information in a suitable format via one or more information feeds to the rules engine 150.

Room sensors 140b may be configured to sense and provide information about one or more environmental conditions, or aspects of a person or object to which the sensor is attached (e.g., temperature, humidity, motion, door or window security, ambient light conditions, location, acceleration, orientation, etc.)

Communication devices 140d may also function as a source of clinical or call context information, such as identifying users of the devices (i.e., caregivers) in proximity to a patient. In some embodiments, the one or more sensors/sources 140a-140d may be configured with, or may communication with a device configured with, a processor and a wired or wireless communication capability to communicate sensed information in a suitable format over a wired or wireless communication links 141a-141d.

The rules engine 150 may include one or more server computing devices configured to receive clinical information via various information feeds from other network elements such as the staffing server 110, the EMR server 120, and the one or more sensors/sources 140a-140d. In various embodiments, the various network elements (e.g., the staffing server 110, the EMR server 120, and the one or more sensors/sources 140a-140d) may be configured to send information to the rules engine 150 in an unsolicited manner (e.g., without requiring a query or another message soliciting information).

By receiving information feeds from the other network elements, the rules engine 150 may avoid interfering with or otherwise altering the normal function and efficiency of the other network elements. For example, the rules engine 150 may not alter electronic medical records stored on the EMR server 120, but rather may receive information periodically provided by the EMR server 120 and stored on the rules engine 150.

The rules engine 150 may be configured to associate certain portions or element(s) of the clinical information with one or more event identifiers for use in generating call context information for an event identifier associated with a particular communication request (i.e., call). Further, the rules engine 150 may be configured to provide the call context information to a called communication device 102, 104, e.g., when a communication request is sent to a communication device 102, 104, as further described below.

In some embodiments, the rules engine 150 may be configured to receive voice commands and to generate message rules based on information in the voice commands. In some embodiments, the rules engine 150 may be configured to receive structured information from another server device, such as the voice server 130b, and to generate message rules based on such structured information. In some embodiments, the rules engine 150 may be configured with an adapter function to add one or more rule template fields, to map information to a rule template field, and to generate a message rule. The rules engine 150 may be configured to monitor patient events to determine whether a generated message rule has been met, and may cause a message to be sent to a communication device 102, 104 (e.g., via the messaging server 130a or the voice communications server 130b) in response to determining that the message rule has been met.

The communication links 111, 114, 121, 124, 131a-134, and 141a-141d may include wired or wireless communication links. Wired communication links may include, for example, twisted pair cable, coaxial cable or fiber optic cable, or combinations thereof. Wireless communication links may include a radio frequency, microwave, infrared, or other similar signal. Wireless communication links may include a plurality of carrier signals, frequencies, or frequency bands, each of which may include a plurality of logical channels. For example, wireless communication links may be established over a Wi-Fi local area wireless communication network.

Other network elements may be present in a communication system 100 system to facilitate communications are omitted for clarity, including additional access points, processing nodes, routers, gateways, and other network elements, as well as physical and/or wireless data links for carrying signals among the various network elements.

Figure 2:
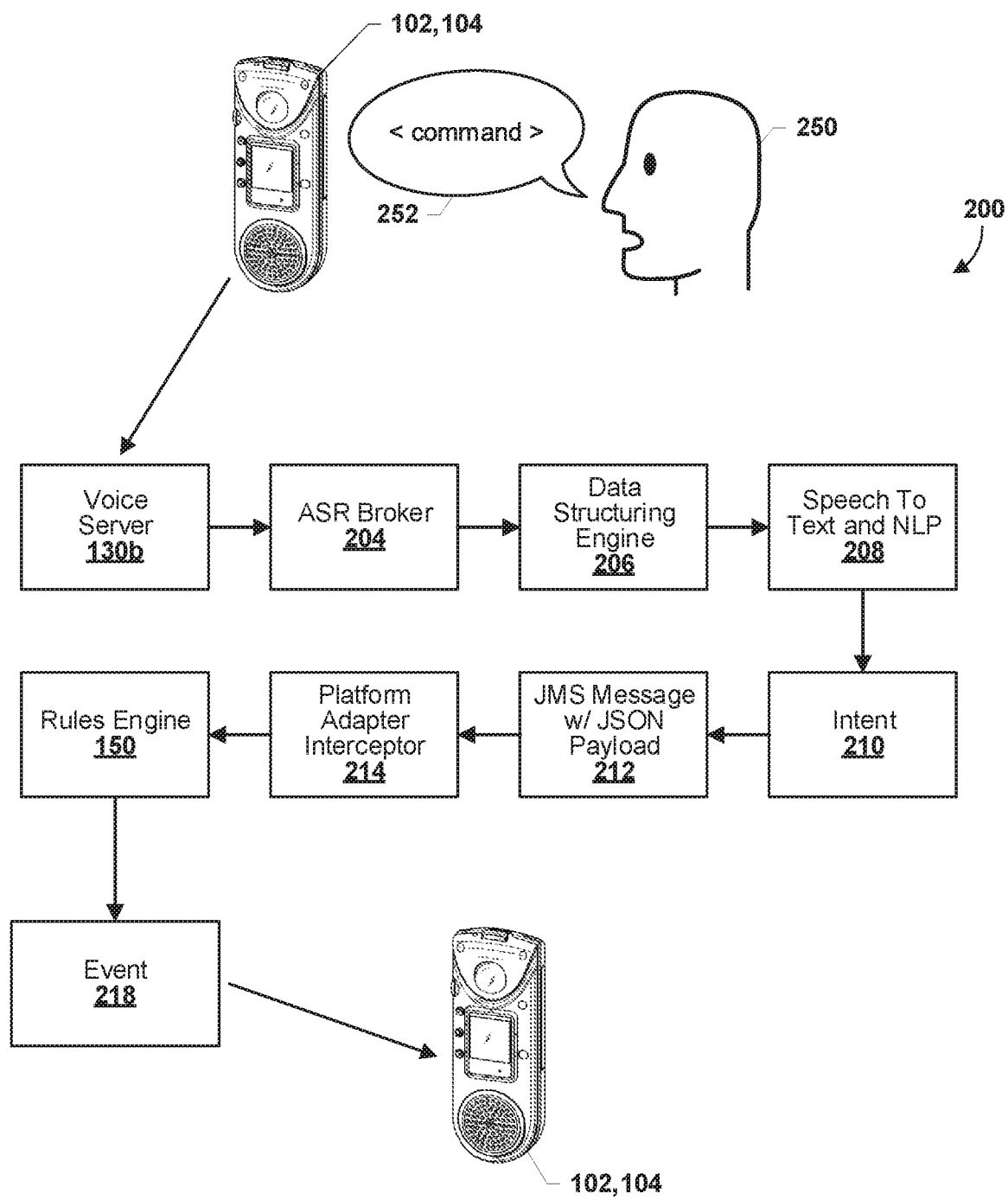
FIG. 2 is a conceptual block diagram illustrating a workflow suitable for use in various embodiments.

FIG. 2 is a conceptual block diagram illustrating a workflow 200 suitable for use in various embodiments. With reference to FIGS. 1 and 2, the workflow 200 may be implemented in hardware components and/or software components of the communication device (e.g., 102, 104) and one or more server devices (e.g., 110, 120, 130a, 130b, 150), the operation of any of which may be controlled by one or more processors (a "processor").

In some embodiments, the communication device 102, 104 may receive a spoken command 252 uttered by a user 250. The communication device 102, 104 may convert the spoken command to a digital form, and may transmit the spoken command (e.g., as a file, a bitstream, or another suitable transmission) to a server device, such as the voice server 130b. An automatic speech recognition broker 204 (e.g., configured in the voice server 130b or another server device) may receive the spoken command, and may provide the spoken command to a data structuring engine 206 (e.g., DialogFlow), that may convert the sound of the spoken command into structured data. A speech-to-text and natural language processing (NLP) function 208 may parse the structured data.

An intent function 210 may receive the structured and parsed data and may determine an intent for the spoken command. In some embodiments, the intent function 210 may perform intent classification to match the structured and parsed data to one of a plurality of intent structures, categories, or other suitable classifications.

In some embodiments, the intent function 210 may send the determined intent in a message 212 (for example, a Java Message Service (JMS) message with a JavaScript Object Notation (JSON) payload) to platform adapter interceptor function ("adapter function") 214. In some embodiments, the adapter function 214 may be configured in a server device such as the rules engine 150. In some embodiments, the adapter function 214 may map elements (e.g., information elements) from the intent to rule template fields. The adapter function 214 may provide a rule template with elements mapped to the rule template fields to the rules engine 150. The rules engine 150 may add this rule to a rules database and may determine whether the generated message rule has been met (for example, by monitoring patient events, or receiving new information or data, such as patient lab orders). In response to determining that the message rule has been met (for example, according to an event 218), the rules engine 150 may send a message to the communication device 102, 104 (e.g., via the message server 130*a* and/or the voice server 130*b*).

Figure 3:
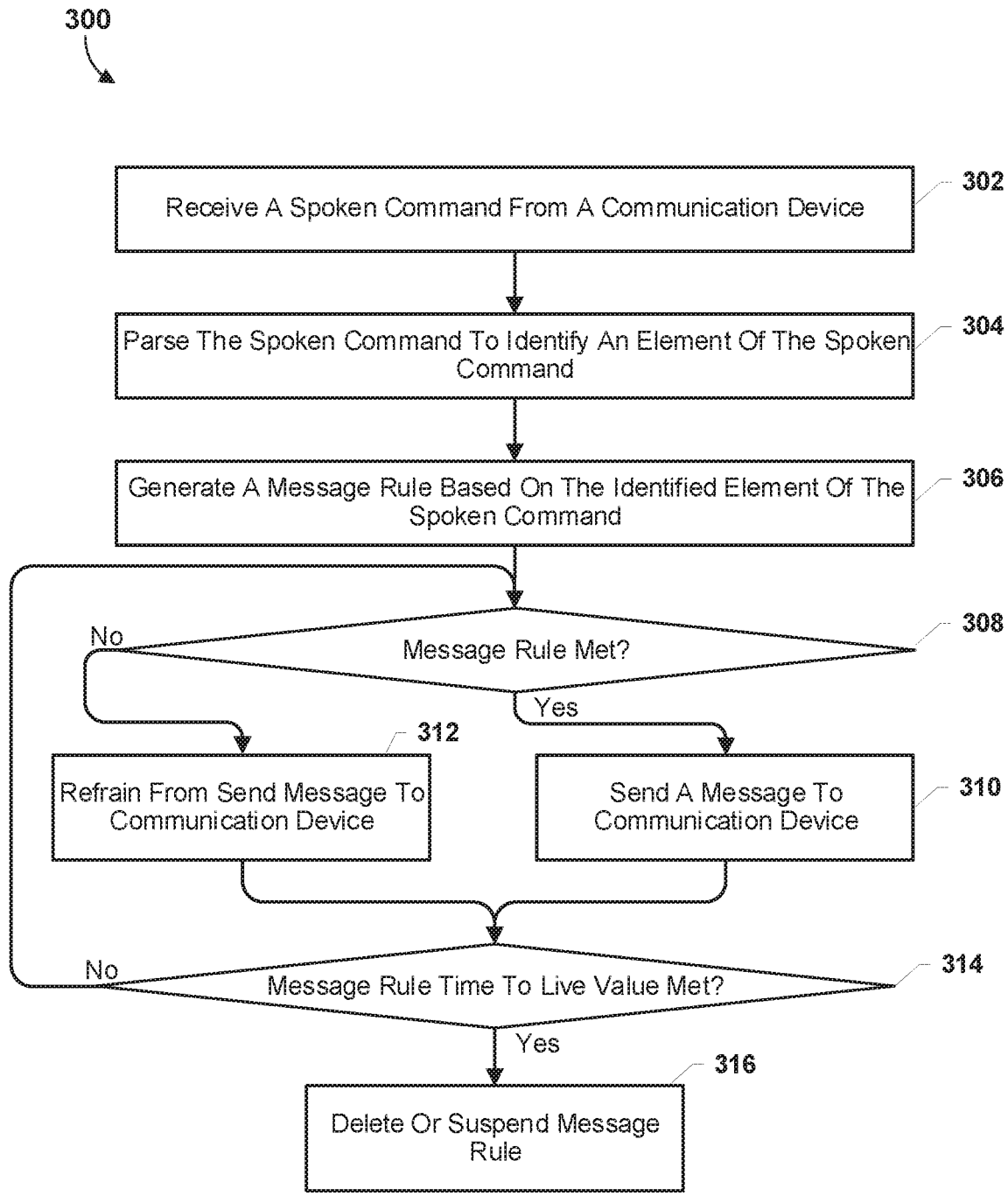
FIG. 3 is a process flow diagram of a voice-activated message filtering rule generation method according to various embodiments.

FIG. 3 illustrates a voice-activated message filtering rule generation method 300 according to various embodiments. With reference to FIGS. 1-3, the method 300 may be implemented in hardware components and/or software components of one or more server devices (e.g., 110, 120, 130*a*, 130*b*, 150), the operation of any of which may be controlled by one or more processors (a "processor").

In block 302, the processor may receive a spoken command from a communication device (e.g., 102, 104). In various embodiments, the processor may receive the spoken command as a digital file, a bitstream, or another suitable form.

In block 304, the processor may parse the spoken command to identify an element of the spoken command. In some embodiments, element of the spoken command may include a subject of the command, an object of the command, an action to be performed, a time period or duration, a time deadline, a threshold condition (such as a vital sign being greater than, less than, or equal to a vital sign threshold, the performance or non-performance of an action, or the occurrence or non-occurrence of an event), a word that functions as a conjunction, preposition, adverb, qualifier, modifier, or emphasizer, or another suitable element.

In block 306, the processor may generate a message rule based on the identified element of the spoken command. In some embodiments, the message rule may be stored in a rules engine (e.g., 150). In some embodiments, the processor may generate a message rule that includes a patient event. In some embodiments, the processor may generate a message rule that includes a patient event and a patient event threshold. In some embodiments, the processor may generate a message rule that includes a patient event and a qualifier of the patient event.

In determination block 308, the processor may determine whether the generated message rule has been met. In some embodiments, the processor may receive information related to a patient event, and using the received patient event information may determine whether the generated message rule has been met. In some embodiments the processor may receive the patient event information in a message from an ADT feed or another suitable message and/or message source.

In response to determining that the generate message rule has been met (i.e., determination block 308="Yes"), the processor may send a message to the communication device in block 310. In some embodiments, the processor may send the message via a server device, such as the message server 130*a* or the voice server 130*b*.

In response to determining that the generate message rule has been met (i.e., determination block 308="Yes"), the processor may send a message to the communication device in block 310.

In response to determining that the generate message rule has not been met (i.e., determination block 308="No"), the processor may refrain from sending the message to the communication device in block 312.

Following the operations of block 310 or block 312, the processor may determine whether a time to live associated with the message rule has been met in determination block 314.

In response to determining that the time to live associated with the message rule has not been met (i.e., determination block 314="No"), the processor may continue to determine whether the message rule is met in determination block 308.

In response to determining that the time to live associated with the message rule has been met (i.e., determination block 314="Yes"), the processor may delete or suspend the message rule in block 316.

In some embodiments, a message rule may be saved for later use. In some embodiments, a message rule may be saved with a label, tag, or nickname for convenient identification and retrieval. The processor may recall and activate a saved rule. For example, based on a voice command such as "Activate alert Lisa Riley high BP," the processor may recall a previously saved message rule "Alert me when Lisa Riley's systolic blood pressure exceeds 180."

FIGS. 4A-4I illustrate operations 400*a*-400*i* that may be performed as part of the voice-activated message filtering rule generation method 300 according to various embodiments. With reference to FIGS. 1-4I, the operations 400*a*-400 is may be implemented in hardware components and/or software components of one or more server devices (e.g., 110, 120, 130*a*, 130*b*, 150), the operation of any of which may be controlled by one or more processors (a "processor").

Figure 4A:
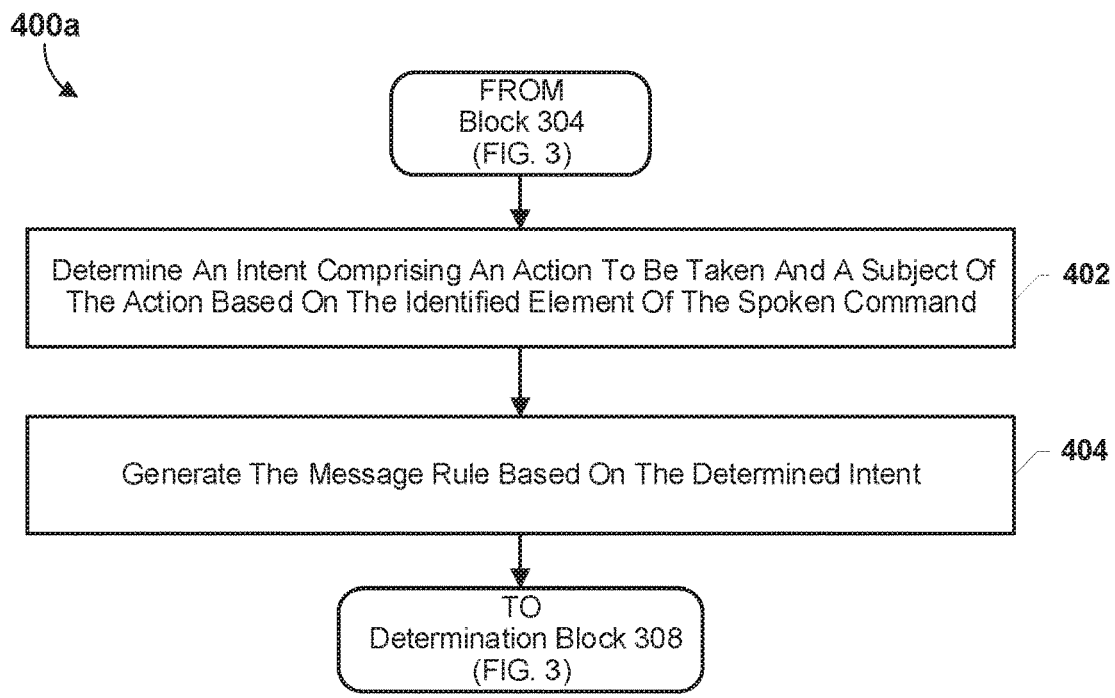
FIGS. 4A-4I illustrate operations that may be performed as part of the voice-activated message filtering rule generation method according to some embodiments.

Referring to FIG. 4A, following the operations of block 304 of the method 300 (FIG. 3), the processor may determine an intent that includes an action to be taken and a subject of the action based on the identified element of the spoken command in block 402. In some embodiments, an action to be taken may include sending a message such as a notification or an alert to a communication device (e.g., 102, 104). In some embodiments, a subject of the action may include a condition such as the occurrence of a patient event. For example, the condition may include a vital sign meeting a threshold value, the performance of an action related to the patient by a caregiver, the expiration of a time interval (e.g., 15 minute intervals between reports of a patient condition), or another suitable condition.

In block 404, the processor may generate a message rule based on the identified element of the spoken command and the determined intent. In some embodiments, the processor may store the generated message rule in a memory device.

The processor may then perform the operations of determination block 308 of the method 300 (FIG. 3) as described.

Figure 4B:
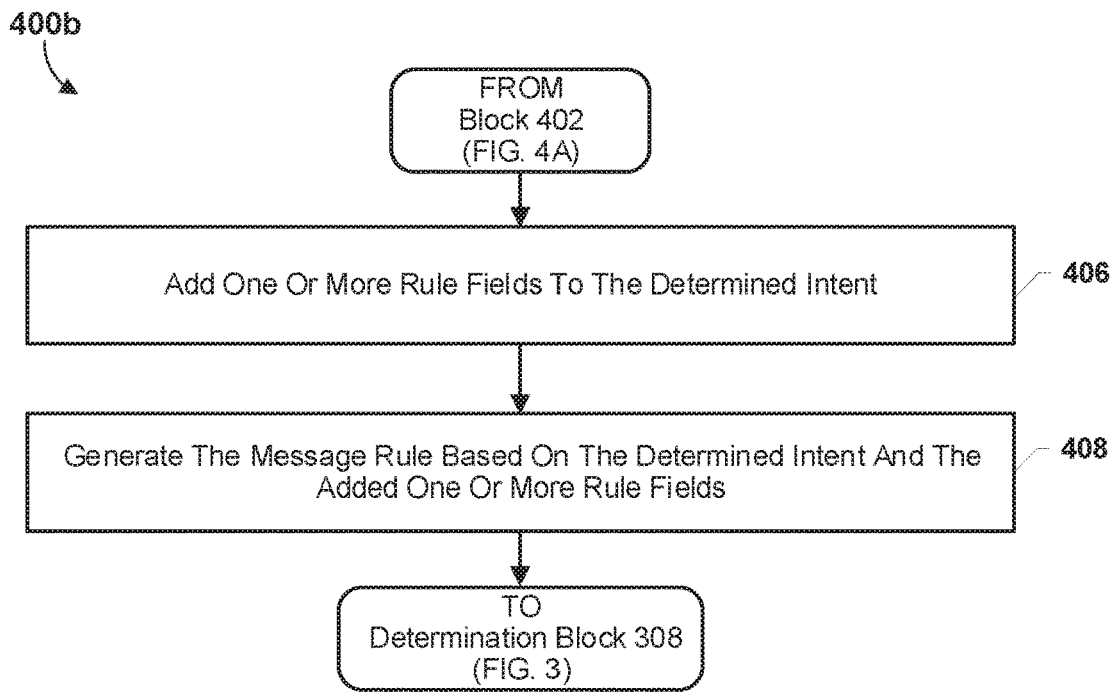

Referring to FIG. 4B, following the operations of block 402 (FIG. 4A), the processor may add one or more rule fields to the determined intent in block 406. In some embodiments, the rule fields may provide additional information that enable the generation of a message rule based on the determined intent. In some embodiments, the rule fields may include additional information, such as a symbol or code, that that enable the generation of a message rule based on the determined intent.

In block 408, the processor may generate the message rule based on the determined intent and the added one or more rule fields.

The processor may then perform the operations of determination block 308 of the method 300 (FIG. 3) as described.

Figure 4C:
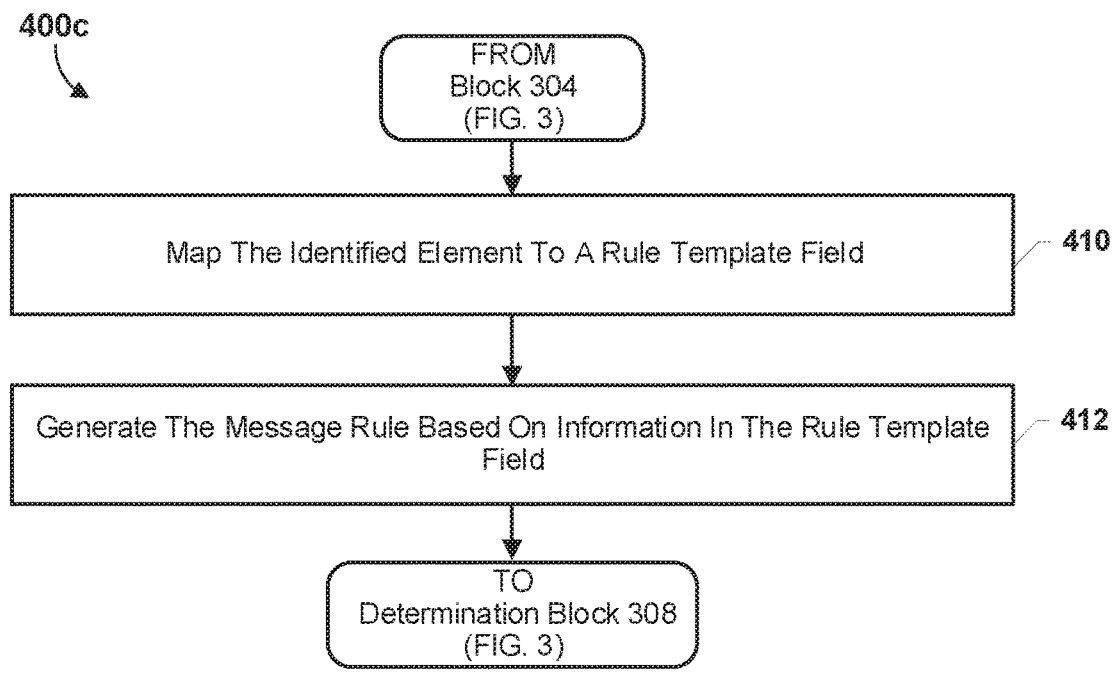

Referring to FIG. 4C, following the operations of block 304 of the method 300 (FIG. 3), the processor may map the identified element to a rule template field in block 410. In some embodiments, the processor may map a patient vital sign identifier to a rule template field. In some embodiments, the processor may map a comparator to a rule template field. In some embodiments, the processor may map a patient vital sign value to a rule template field. In some embodiments, the processor may apply a customized mapping of the identified element and the rule template field.

In block 412, the processor may generate the message rule based in part on information in the rule template field.

The processor may then perform the operations of determination block 308 of the method 300 (FIG. 3) as described.

Figure 4D:
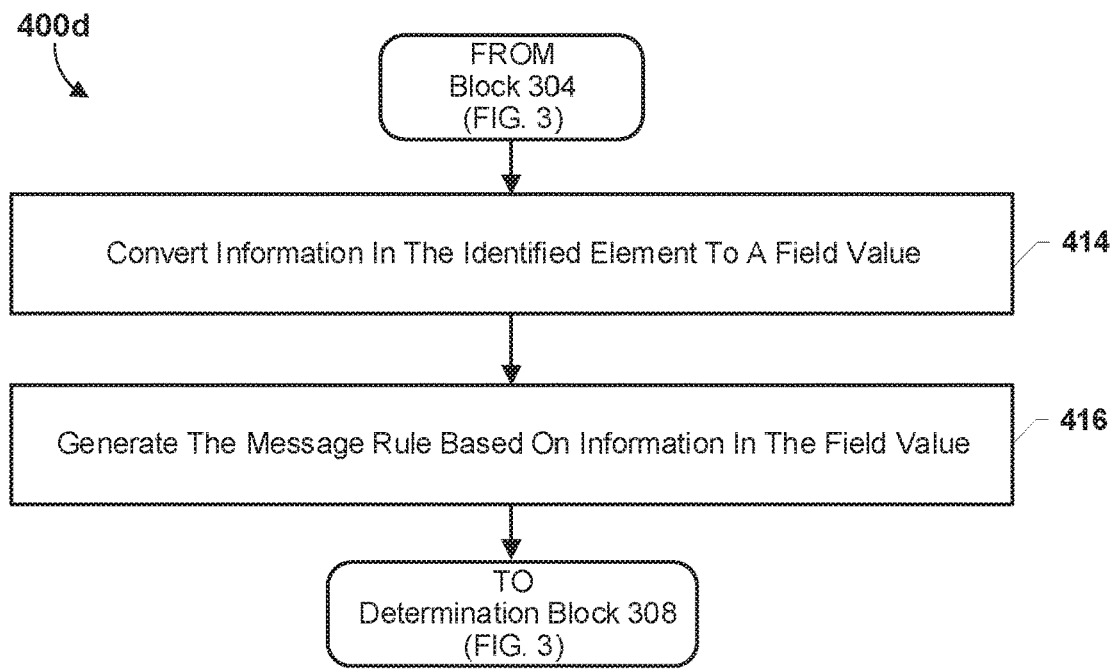

Referring to FIG. 4D, following the operations of block 304 of the method 300 (FIG. 3), the processor may convert information in the identified element to a field value in block 414. In some embodiments, the processor may map the field value to a rule template field.

In block 416, the processor may generate the message rule based in part on information in the field value.

The processor may then perform the operations of determination block 308 of the method 300 (FIG. 3) as described.

Figure 4E:
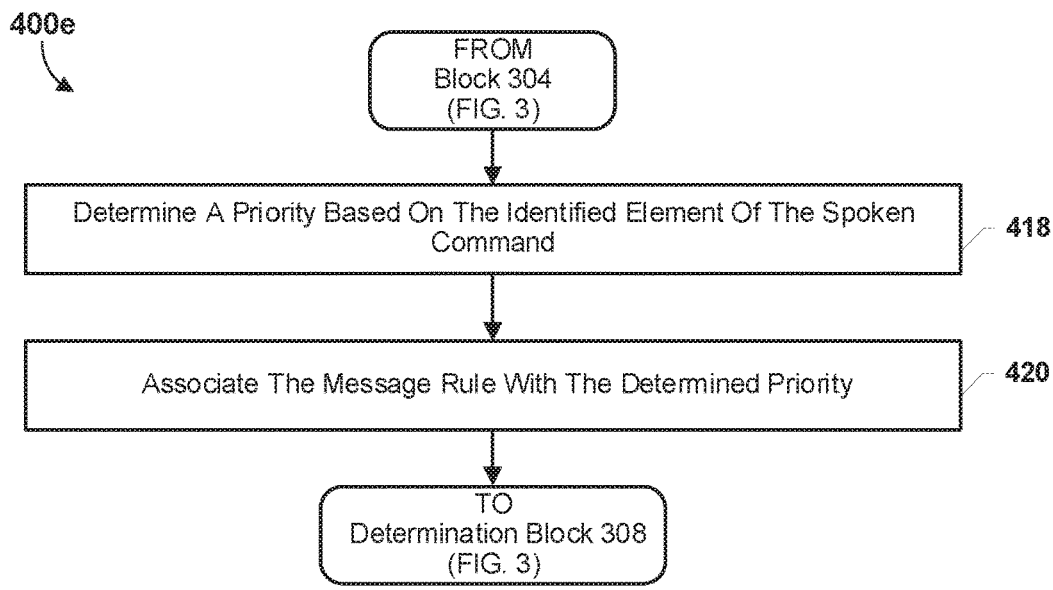

Referring to FIG. 4E, following the operations of block 304 of the method 300 (FIG. 3), the processor may determine a priority based on the identified element of the spoken command in block 418. For example, as noted above, based on the presence of a priority indicator in an element, such as "urgently" or "right away," the server device may determine an indication of a relatively higher priority (e.g., "urgent," or a numeric or symbolic expression thereof) as compared to a relatively lower priority (e.g., "normal," or a numeric or symbolic expression thereof).

In block 420, the processor may associate the message rule with the determined priority. In some embodiments, based on the priority, the server device may associate a priority with a message, notification, or alert that the server device later sends to the communication device, for example, as part of the operations of block 310 of the method 300 (FIG. 3).

The processor may then perform the operations of determination block 308 of the method 300 (FIG. 3) as described.

Figure 4F:
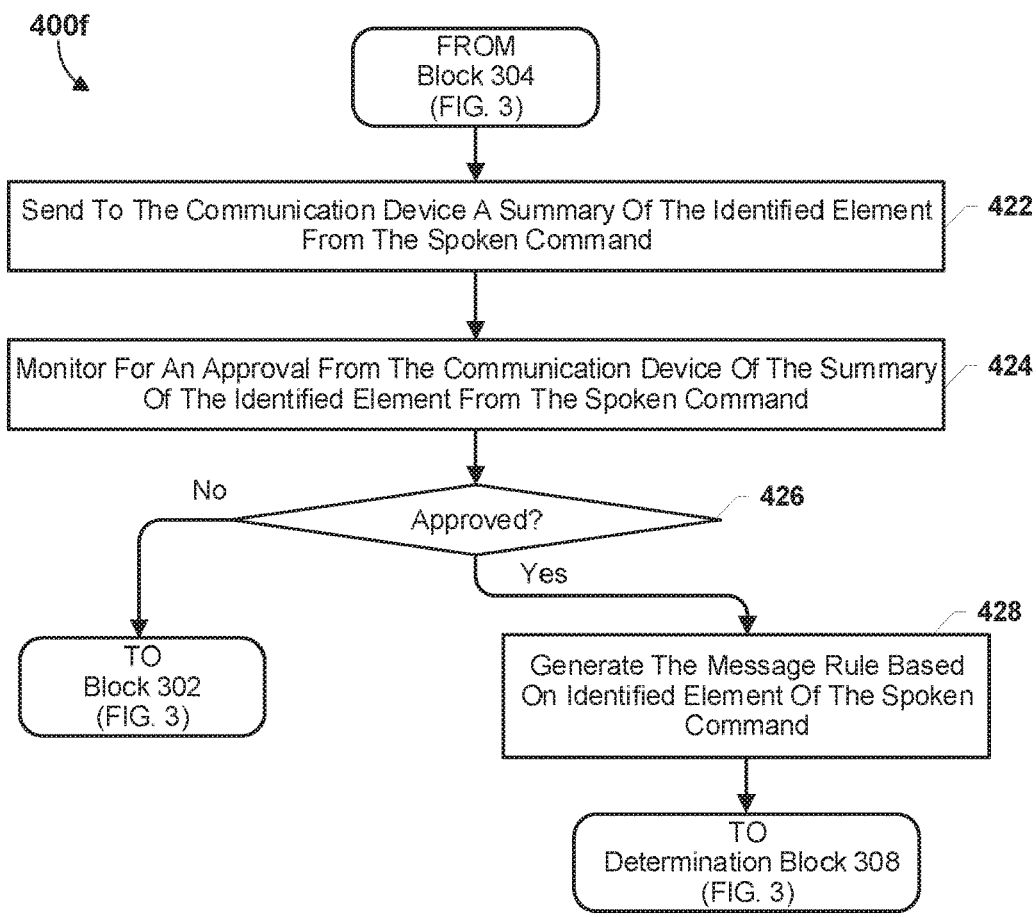

Referring to FIG. 4F, following the operations of block 304 of the method 300 (FIG. 3), the processor may send to the communication device a summary of the identified element from the spoken command in block 422.

In block 424, the processor may monitor for an approval from the communication device of the summary of the identified element from the spoken command.

In determination block 426, the processor may determine whether the approval of the summary of the identified element has been received.

In response to determining that the approval of the summary of the identified element has not been received (or that a disapproval of the summary has been received) (i.e., determination block 426="No"), the processor may perform the operations of block 302 of the method 300 (FIG. 3) as described.

In response to determining that the approval of the summary of the identified element has been received (i.e., determination block 426="Yes"), the processor may generate the message rule based on identified elements of the spoken command in block 428.

The processor may then perform the operations of determination block 308 of the method 300 (FIG. 3) as described.

Figure 4G:
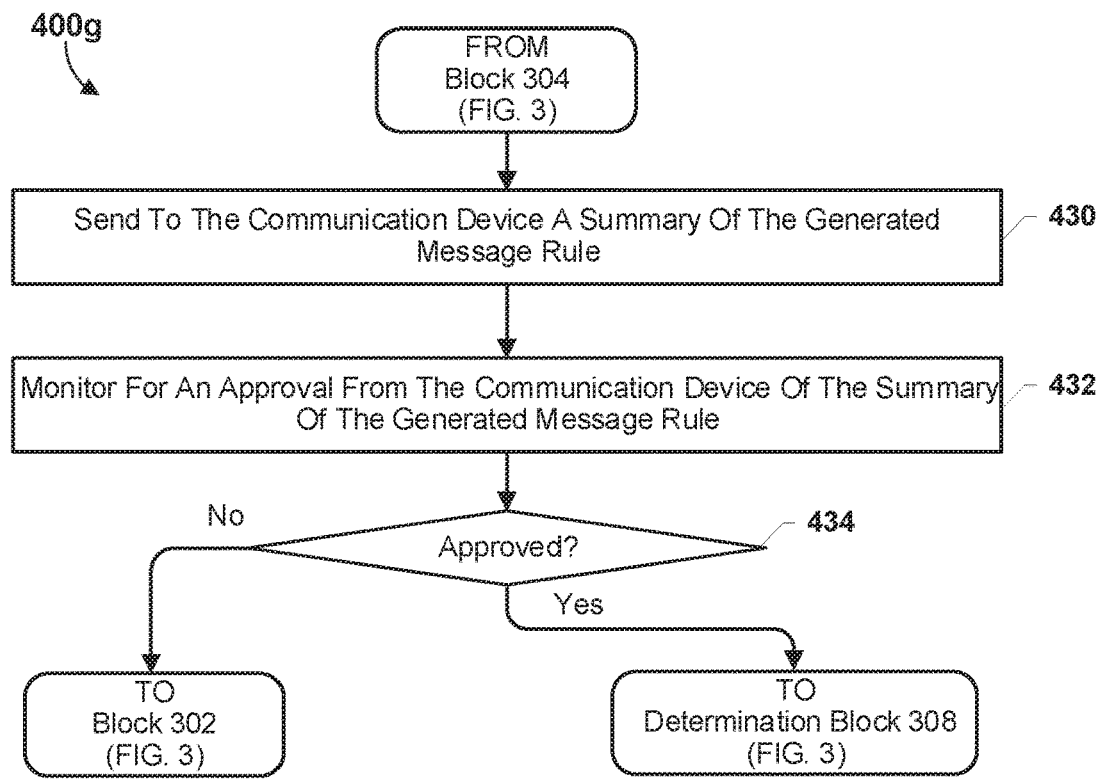

Referring to FIG. 4G, following the operations of block 304 of the method 300 (FIG. 3), the processor may send to the communication device a summary of the generated message rule in block 430.

In block 432, the processor may monitor for an approval from the communication device of the summary of the generated message rule.

In determination block 434, the processor may determine whether the approval of the summary of the generated message rule has been received.

In response to determining that the approval of the summary of the generated message rule has not been received (or that a disapproval of the summary has been received) (i.e., determination block 434="No"), the processor may perform the operations of block 302 of the method 300 (FIG. 3) as described.

In response to determining that the approval of the summary of the generated message rule has been received (i.e., determination block 434="Yes"), the processor may generate the message rule based on identified elements of the spoken command in block 436.

The processor may then perform the operations of determination block 308 of the method 300 (FIG. 3) as described.

Figure 4H:
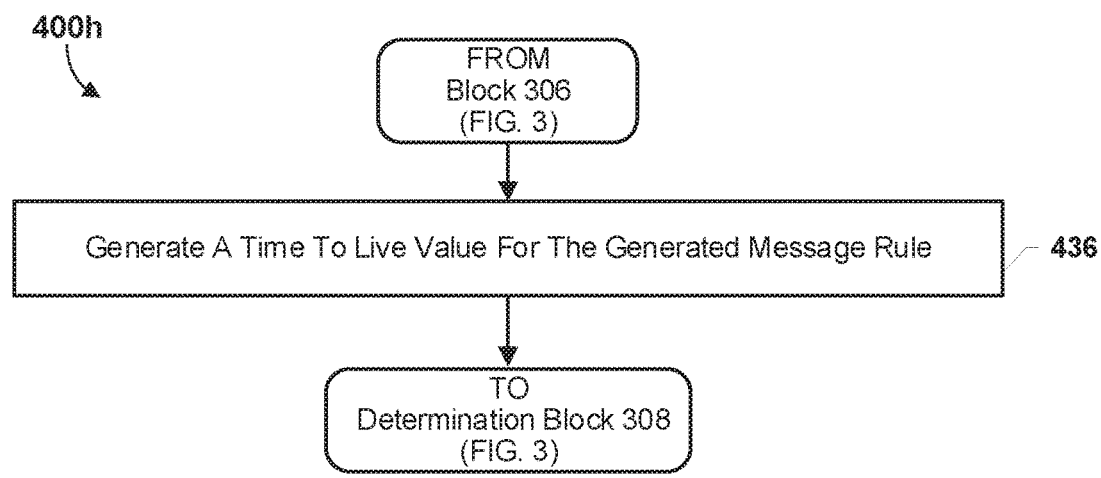
Figure 4I:
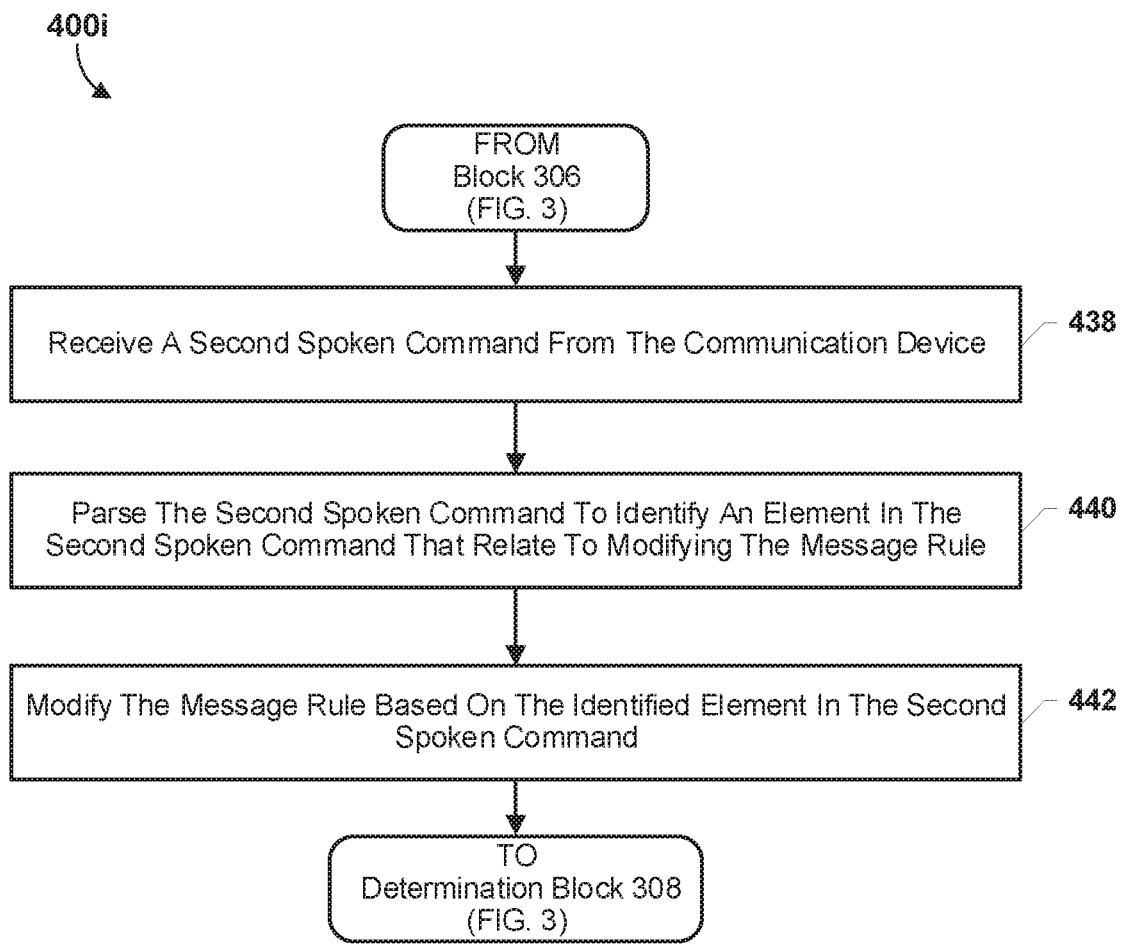

Referring to FIG. 4H, following the operations of block 306 of the method 300 (FIG. 3), the processor may generate a time to live value for the generated message rule in block 436. n some embodiments, the server device may generate a time to live value that indicates a duration or time period for the generated message rule. In some embodiments, the processor may generate the time to live value based on an identified element in the spoken command.

The processor may then perform the operations of determination block 308 of the method 300 (FIG. 3) as described.

Referring to FIG. 4H, following the operations of block 306 of the method 300 (FIG. 3), the processor may receive a second spoken command from the communication device in block 438.

In block 440, the processor may parse the second spoken command to identify an element in the second spoken command that relate to modifying the message rule.

In block 442, the processor may modify the message rule based on the identified element in the second spoken command.

The processor may then perform the operations of determination block 308 of the method 300 (FIG. 3) as described.

FIG. 5 illustrates a communication device 500 suitable for use in various embodiments. With reference to FIGS. 1-5, in some embodiments, the communication device 500 may include a voice communications badge device. The communication device 500 may include a housing 502 that encloses various components. The communication device 500 may include a microphone 510, a speaker 506, and a display device 504 such as a liquid crystal display (LCD). Various information may be displayed on the display device 504, such as data for reviewing text messages and pages received by the communication device 500 and/or data to facilitate the operation of the communication device 500. The microphone 510 and speaker 506 may also be used for voice communications. In some embodiments, the voice communication device 500 may further include an amplifier that amplifies the signals provided to/from the microphone and speaker.

The communication device 500 may further include an input device 514 that permits a user to configure and operate the communication device 500. In some embodiments, the input device 514 may be a jog switch that may be a spring-loaded compound-action switch that supports three momentary actions. In such embodiments, the switch may be pressed inwards as an ordinary push button. In some embodiments, the input device 514 may also be rotated in either direction and/or may be a touch button location in particular location (e.g., on the front of the communication device 500) that may be pushed or touched to activate the same functions and operations being activated by the jog switch. The communication device 500 may also include an on/off switch 516 and a status indicator (e.g., a light emitting diode (LED) that may be capable of displaying one or more different colors to signal the operational status of the communication device 500, etc.). In some embodiments, the communication device 500 may optionally include a headset jack that enables the user to plug in an external microphone/speaker headset, such as an ear bud.

Internally, the communication device 500 may include a central processing unit (CPU) or processor 550 that controls the operation of the components of the communication device 500. For example, the processor 550 may control the operations of the microphone 510 and the speaker 506 so that the communication device 500 may exchange voice communications, commands, and/or responses with remote devices (e.g., a voice communications server, etc.). The communication device 500 may further include a non-volatile memory device 552 so that data stored in the communication device 500 (such as settings, messages, and other data structures) are not lost when the communication device 500 is powered down. For example, the non-volatile memory device 552 may be a storage unit or other memory device configured to store at least a factory-assigned a unique physical media access control (MAC) address or unique wireless device address. The communication device 500 may also include a wireless transceiver 554 (e.g., an appropriate strength 802.5 transceiver, etc.) and an antenna 556 that may be used for wireless communications with various access points or with other devices (e.g., other communication devices, etc.). In some embodiments, the antennae 556 may be built into an exterior clip of the communication device 500 or may reside completely within the housing 502 of the communication device 500.

The communication device 500 may further include a pager receiver 560 that operates with the antenna 556 to receive text messages/pages within the coverage of any global paging service network. The communication device 500 may further comprise a digital signal processor (DSP) 562 and an audio codec 564 for processing incoming speech from the microphone 510 and for generating the voice signals generated by the speaker 506. For example, the DSP 562 and audio codec 564 may be capable of compressing digital voice data to reduce the amount of digital data used to communicate the voice commands to the server. The communication device 500 may include a power source 558, such as a removable, rechargeable battery that may include protection and charge management circuitry to prevent over-charging. For example, the energy source 558 may be a replaceable, rechargeable lithium polymer or lithium ion battery that fits on or in the housing 502. The various components may be connected via a bus or other similar linkage or connectivity.

Exemplary descriptions of various voice communications badge devices suitable for use in various embodiments may also be found in commonly-held patent applications, including U.S. Pat. No. 6,892,083 entitled "Voice-Controlled Wireless Communications System and Method," U.S. Pat. No. 8,098,806 entitled "Non-User-Specific Wireless Communication System and Method," and U.S. Design Pat. D679,673, the content of all of which are incorporated herein for descriptions of various communication device components.

Figure 6:
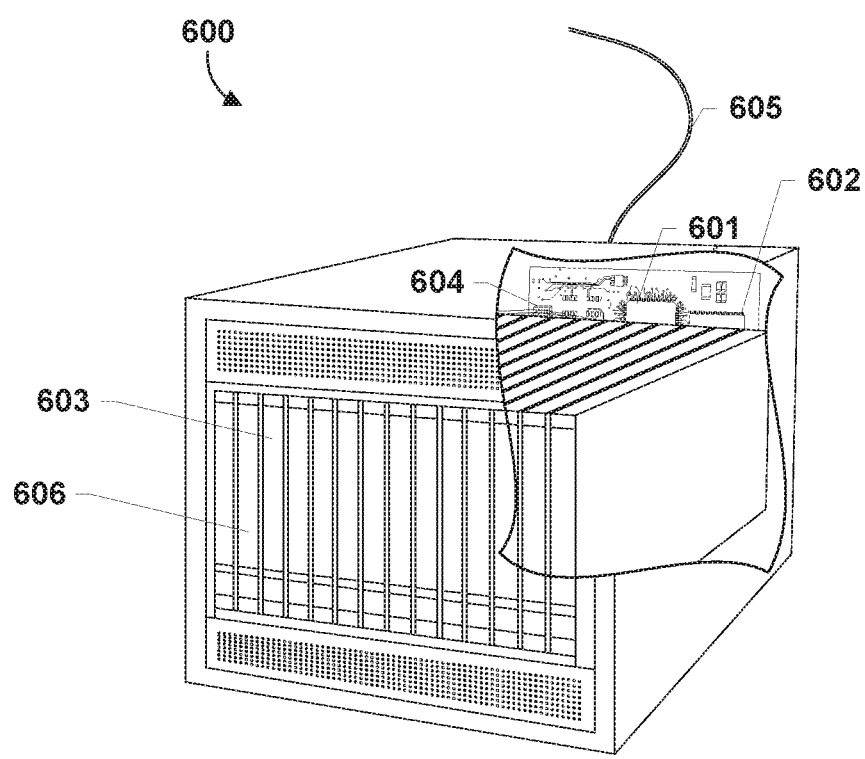
FIG. 6 illustrates a server device suitable for use in various embodiments.

FIG. 6 illustrates a server device 600 suitable for use in various embodiments. With reference to FIGS. 1-6, various embodiments may employ the server device 600 as a network element of a communication system (e.g., the communication system 100). Examples of network elements that may be implemented in a server device, or as a logical service in a server device, include the staffing server 60, the EMR server 60, the messaging server 130a, the voice communications server 130b, and the rules engine 150. The server device 600 may include a processor 601 coupled to volatile memory 602 and a large capacity nonvolatile memory, such as a disk drive 603. The server device 600 may also include a peripheral memory access device such as a floppy disc drive, compact disc (CD) or digital video disc (DVD) drive 606 coupled to the processor 601. The server device 600 may also include network access ports 604 (or interfaces) coupled to the processor 601 for establishing data connections with a network 605, such as the Internet and/or a local area network coupled to other system computers, including wireless access points (e.g., 106, 108 in FIG. 1) for sending and receiving electromagnetic radiation that may be connected to a wireless communication link. The server device 600 may include additional access ports, such as USB, Firewire, Thunderbolt, and the like for coupling to peripherals, external memory, or other devices.

The various processors described herein may be any programmable microprocessor, microcomputer or multiple processor chip or chips that can be configured by software instructions (applications) to perform a variety of functions, including the functions of the various embodiments described herein. In the various devices, multiple processors may be provided, such as one processor dedicated to wireless communication functions and one processor dedicated to running other applications. Typically, software applications may be stored in internal memory before they are accessed and loaded into the processors. The processors may include internal memory sufficient to store the application software instructions. In many devices the internal memory may be a volatile or nonvolatile memory, such as flash memory, or a mixture of both. For the purposes of this description, a general reference to memory refers to memory accessible by the processors including internal memory or removable memory plugged into the various devices and memory within the processors.

The foregoing method descriptions and the process flow diagrams are provided merely as illustrative examples and are not intended to require or imply that the operations of the various embodiments must be performed in the order presented. Accordingly, the order of operations in the foregoing embodiments may be performed in any order. Words such as "thereafter," "then," "next," etc. are not intended to limit the order of the operations; these words are simply used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm operations described in connection with the embodiments disclosed herein may be implemented as electronic hardware, computer software, or combinations of both. To clearly illustrate this interchangeability of hardware and software, various illustrative components, blocks, modules, circuits, and operations have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The hardware used to implement the various illustrative logics, logical operations, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some operations or methods may be performed by circuitry that is specific to a given function.

In one or more exemplary embodiments, the functions described may be implemented in hardware, software, firmware, or any combination thereof. If implemented in software, the functions may be stored on or transmitted over as one or more instructions or code on a non-transitory processor-readable, computer-readable, or server-readable medium or a non-transitory processor-readable storage medium. The operations of a method or algorithm disclosed herein may be embodied in a processor-executable software module or processor-executable software instructions which may reside on a non-transitory computer-readable storage medium, a non-transitory server-readable storage medium, and/or a non-transitory processor-readable storage medium. In various embodiments, such instructions may be stored processor-executable instructions or stored processor-executable software instructions. Tangible, non-transitory computer-readable storage media may be any available media that may be accessed by a computer. By way of example, and not limitation, such non-transitory computer-readable media may comprise RAM, ROM, EEPROM, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray Disc® where disks usually reproduce data magnetically, while discs reproduce data optically with lasers. Combinations of the above should also be included within the scope of non-transitory computer-readable media. Additionally, the operations of a method or algorithm may reside as one or any combination or set of codes and/or instructions on a tangible, non-transitory processor-readable storage medium and/or computer-readable medium, which may be incorporated into a computer program product.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

What is claimed is:

1. A voice-activated message filtering rule generation method performed by a processor of a server device, comprising:
   receiving a spoken command from a communication device;
   parsing the spoken command to identify an element of the spoken command;
   sending to the communication device a summary of the identified element of the spoken command;
   monitoring for an approval from the communication device of the summary of the identified element of the spoken command;
   generating a message rule based on the identified element of the spoken command, wherein generating the message rule based on the identified element of the spoken command comprises generating the message rule based on the identified element of the spoken command in response to receiving the approval from the communication device of the summary of the identified element of the spoken command;
   determining whether the generated message rule has been met; and
   sending a message to the communication device in response to determining that the message rule has been met.

2. The method of claim 1, further comprising determining an intent comprising an action to be taken and a subject of the action based on the identified element of the spoken command.

3. The method of claim 2, wherein generating the message rule based on the identified element of the spoken command comprises generating the message rule based on the determined intent.

4. The method of claim 2, wherein generating the message rule based on the identified element of the spoken command comprises:
   adding one or more rule fields to the determined intent; and
   generating the message rule based on the determined intent and the added one or more rule fields.

5. The method of claim 1, wherein generating the message rule based on the identified element of the spoken command comprises generating the message rule comprising a patient event.

6. The method of claim 1, wherein generating the message rule based on the identified element of the spoken command comprises generating the message rule comprising a patient event and a patient event threshold.

7. The method of claim 1, wherein generating the message rule based on the identified element of the spoken command comprises generating the message rule comprising a patient event and a qualifier of the patient event.

8. The method of claim 1, further comprising refraining from sending the message to the communication device in response to determining that the message rule has not been met.

9. The method of claim 1, wherein generating the message rule based on the identified element of the spoken command comprises:
   mapping the identified element to a rule template field; and
   generating the message rule based on information in the rule template field.

10. The method of claim 9, wherein
   mapping the identified element to the rule template field comprises converting information in the identified element to a field value, and
   generating the message rule based on information in the rule template field comprises generating the message rule based on information in the field value.

11. The method of claim 9, wherein mapping the identified element to the rule template field comprises mapping a patient vital sign identifier to the rule template field.

12. The method of claim 9, wherein mapping the identified element to the rule template field comprises mapping a comparator to the rule template field.

13. The method of claim 9, wherein mapping the identified element to the rule template field comprises mapping a patient vital sign value to the rule template field.

14. The method of claim 9, wherein mapping the identified element to the rule template field comprises applying a customized mapping of the identified element and the rule template field.

15. The method of claim 1, further comprising identifying a further element of the spoken command, determining a priority based on the identified further element of the spoken command, and associating the message rule with the determined priority.

16. The method of claim 15, wherein determining the priority based on the identified further element of the spoken command comprises determining an indication of relatively higher priority as compared to a relatively lower priority.

17. The method of claim 1, further comprising:
sending to the communication device a summary of the generated message rule; and
monitoring for an approval from the communication device of the summary of the generated message rule,
wherein determining whether the generated message rule has been met comprises determining whether the generated message rule has been met in response to receiving an approval from the communication device of the summary of the generated message rule.

18. The method of claim 1, further comprising:
generating a time to live value for the generated message rule; and
deleting the message rule after the time to live value is met.

19. The method of claim 1, further comprising:
receiving a second spoken command from the communication device;
parsing the second spoken command to identify an element in the second spoken command that relates to modifying the message rule; and
modifying the message rule based on the identified element in the second spoken command.

20. A server device, comprising:
at least a processor configured with processor executable instructions to perform operations comprising:
receiving a spoken command from a communication device;
parsing the spoken command to identify an element of the spoken command;
sending to the communication device a summary of the identified element of the spoken command;
monitoring for an approval from the communication device of the summary of the identified element the spoken command;
generating a message rule based on the identified element of the spoken command, wherein generating the message rule based on the identified element of the spoken command comprises generating the message rule based on the identified element of the spoken command in response to receiving the approval from the communication device of the summary of the identified element of the spoken command;
determining whether the generated message rule has been met; and
sending a message to the communication device in response to determining that the message rule has been met.

21. The server device of claim 20, wherein the processor is configured with processor executable instructions to perform operations comprising determining an intent comprising an action to be taken and a subject of the action based on the identified element of the spoken command.

22. The server device of claim 21, wherein the processor is configured with processor executable instructions to perform operations such that generating the message rule based on the identified element of the spoken command comprises generating the message rule based on the determined intent.

23. The server device of claim 21, wherein the processor is configured with processor executable instructions to perform operations such that generating the message rule based on the identified element of the spoken command comprises:
adding one or more rule fields to the determined intent; and
generating the message rule based on the determined intent and the added one or more rule fields.

24. The server device of claim 20, wherein the processor is configured with processor executable instructions to perform operations such that generating the message rule based on the identified element of the spoken command comprises generating the message rule comprising a patient event.

25. The server device of claim 20, wherein the processor is configured with processor executable instructions to perform operations such that generating the message rule based on the identified element of the spoken command comprises generating the message rule comprising a patient event and a patient event threshold.

26. The server device of claim 20, wherein the processor is configured with processor executable instructions to perform operations such that generating the message rule based on the identified element of the spoken command comprises generating the message rule comprising a patient event and a qualifier of the patient event.

27. The server device of claim 20, wherein the processor is configured with processor executable instructions to perform operations further comprising refraining from sending the message to the communication device in response to determining that the message rule has not been met.

28. The server device of claim 20, wherein the processor is configured with processor executable instructions to perform operations such that generating the message rule based on the identified element of the spoken command comprises:
mapping the identified element to a rule template field; and
generating the message rule based on information in the rule template field.

29. The server device of claim 28, wherein the processor is configured with processor executable instructions to perform operations such that:
mapping the identified element to the rule template field comprises converting information in the identified element to a field value, and
generating the message rule based on information in the rule template field comprises generating the message rule based on information in the field value.

30. The server device of claim 28, wherein the processor is configured with processor executable instructions to perform operations such that mapping the identified element to the rule template field comprises mapping a patient vital sign identifier to the rule template field.

31. The server device of claim 28, wherein the processor is configured with processor executable instructions to perform operations such that mapping the identified element to the rule template field comprises mapping a comparator to the rule template field.

32. The server device of claim 28, wherein the processor is configured with processor executable instructions to perform operations such that mapping the identified element to the rule template field comprises mapping a patient vital sign value to the rule template field.

33. The server device of claim 28, wherein the processor is configured with processor executable instructions to perform operations such that mapping the identified element to the rule template field comprises applying a customized mapping of the identified element and the rule template field.

34. The server device of claim 20, wherein the operations additionally comprise identifying a further element of the spoken command, determining a priority based on the identified further element of the spoken command, and associating the message rule with the determined priority.

35. The server device of claim 34, wherein determining the priority based on the identified further element of the spoken command comprises determining an indication of relatively higher priority as compared to a relatively lower priority.

36. The server device of claim 20, wherein the processor is configured with processor executable instructions to perform operations further comprising:
sending to the communication device a summary of the generated message rule; and
monitoring for an approval from the communication device of the summary of the generated message rule,
wherein the processor is configured with processor executable instructions to perform operations such that determining whether the generated message rule has been met comprises determining whether the generated message rule has been met in response to receiving an approval from the communication device of the summary of the generated message rule.

37. The server device of claim 20, wherein the processor is configured with processor executable instructions to perform operations further comprising:
generating a time to live value for the generated message rule; and
deleting the message rule after the time to live value is met.

38. The server device of claim 20, wherein the processor is configured with processor executable instructions to perform operations further comprising:
receiving a second spoken command from the communication device;
parsing the second spoken command to identify an element in the second spoken command that relates to modifying the message rule; and
modifying the message rule based on the identified element in the second spoken command.

39. A non-transitory processor-readable medium having stored thereon processor-executable instruction configured to cause a processing device in a server device to perform operations comprising:
receiving a spoken command from a communication device;
parsing the spoken command to identify an element of the spoken command;
sending to the communication device a summary of the identified element of the spoken command;
monitoring for an approval from the communication device of the summary of the identified element of the spoken command;
generating a message rule based on the identified element of the spoken command, wherein generating the message rule based on the identified element of the spoken command comprises generating the message rule based on the identified element of the spoken command in response to receiving the approval from the communication device of the summary of the identified element of the spoken command;
determining whether the generated message rule has been met; and
sending a message to the communication device in response to determining that the message rule has been met.

40. The non-transitory processor-readable medium of claim 39, wherein the stored processor-executable instructions are configured to cause a processor of a server device to perform operations further comprising determining an intent comprising an action to be taken and a subject of the action based on the identified element of the spoken command.

41. The non-transitory processor-readable medium of claim 40, wherein the stored processor-executable instructions are configured to cause a processor of a server device to perform operations such that generating the message rule based on the identified element of the spoken command comprises generating the message rule based on the determined intent.

42. The non-transitory processor-readable medium of claim 40, wherein the stored processor-executable instructions are configured to cause a processor of a server device to perform operations such that generating the message rule based on the identified element of the spoken command comprises:
adding one or more rule fields to the determined intent; and
generating the message rule based on the determined intent and the added one or more rule fields.

43. The non-transitory processor-readable medium of claim 39, wherein the stored processor-executable instructions are configured to cause a processor of a server device to perform operations such that generating the message rule based on the identified element of the spoken command comprises generating the message rule comprising a patient event.

44. The non-transitory processor-readable medium of claim 39, wherein the stored processor-executable instructions are configured to cause a processor of a server device to perform operations such that generating the message rule based on the identified element of the spoken command comprises generating the message rule comprising a patient event and a patient event threshold.

45. The non-transitory processor-readable medium of claim 39, wherein the stored processor-executable instructions are configured to cause a processor of a server device to perform operations such that generating the message rule based on the identified element of the spoken command comprises generating the message rule comprising a patient event and a qualifier of the patient event.

46. The non-transitory processor-readable medium of claim 39, wherein the stored processor-executable instructions are configured to cause a processor of a server device to perform operations further comprising refraining from sending the message to the communication device in response to determining that the message rule has not been met.

47. The non-transitory processor-readable medium of claim 39, wherein the stored processor-executable instructions are configured to cause a processor of a server device to perform operations such that generating the message rule based on the identified element of the spoken command comprises:
   mapping the identified element to a rule template field; and
   generating the message rule based on information in the rule template field.

48. The non-transitory processor-readable medium of claim 47, wherein the stored processor-executable instructions are configured to cause a processor of a server device to perform operations such that:
   mapping the identified element to the rule template field comprises converting information in the identified element to a field value, and
   generating the message rule based on information in the rule template field comprises generating the message rule based on information in the field value.

49. The non-transitory processor-readable medium of claim 47, wherein the stored processor-executable instructions are configured to cause a processor of a server device to perform operations such that mapping the identified element to the rule template field comprises mapping a patient vital sign identifier to the rule template field.

50. The non-transitory processor-readable medium of claim 47, wherein the stored processor-executable instructions are configured to cause a processor of a server device to perform operations such that mapping the identified element to the rule template field comprises mapping a comparator to the rule template field.

51. The non-transitory processor-readable medium of claim 47, wherein the stored processor-executable instructions are configured to cause a processor of a server device to perform operations such that mapping the identified element to the rule template field comprises mapping a patient vital sign value to the rule template field.

52. The non-transitory processor-readable medium of claim 47, wherein the stored processor-executable instructions are configured to cause a processor of a server device to perform operations such that mapping the identified element to the rule template field comprises applying a customized mapping of the identified element and the rule template field.

53. The non-transitory processor-readable medium of claim 39, wherein the operations additionally comprise identifying a further element of the spoken command, determining a priority based on the identified further element of the spoken command, and associating the message rule with the determined priority.

54. The non-transitory processor-readable medium of claim 53, wherein determining the priority based on the identified further element of the spoken command comprises determining an indication of relatively higher priority as compared to a relatively lower priority.

55. The non-transitory processor-readable medium of claim 39, wherein the stored processor-executable instructions are configured to cause a processor of a server device to perform operations further comprising:
   sending to the communication device a summary of the generated message rule; and
   monitoring for an approval from the communication device of the summary of the generated message rule,
   wherein the stored processor-executable instructions are configured to cause a processor of a server device to perform operations such that determining whether the generated message rule has been met comprises determining whether the generated message rule has been met in response to receiving an approval from the communication device of the summary of the generated message rule.

56. The non-transitory processor-readable medium of claim 39, wherein the stored processor-executable instructions are configured to cause a processor of a server device to perform operations further comprising:
   generating a time to live value for the generated message rule; and
   deleting the message rule after the time to live value is met.

57. The non-transitory processor-readable medium of claim 39, wherein the stored processor-executable instructions are configured to cause a processor of a server device to perform operations further comprising:
   receiving a second spoken command from the communication device;
   parsing the second spoken command to identify an element in the second spoken command that relates to modifying the message rule; and
   modifying the message rule based on the identified element in the second spoken command.

\* \* \* \* \*